US 10,856,898 B2

(12) United States Patent
Matsushita et al.

(10) Patent No.: US 10,856,898 B2
(45) Date of Patent: Dec. 8, 2020

(54) FOREIGN OBJECT REMOVAL DEVICE

(71) Applicant: TERUMO KABUSHIKI KAISHA, Tokyo (JP)

(72) Inventors: Shuhei Matsushita, Hadano (JP); Hiroshi Yagi, Ichinomiya (JP); Junko Kuniyasu, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 328 days.

(21) Appl. No.: 15/699,993

(22) Filed: Sep. 8, 2017

(65) Prior Publication Data
US 2017/0367719 A1  Dec. 28, 2017

Related U.S. Application Data

(63) Continuation of application No. PCT/JP2016/057547, filed on Mar. 10, 2016.

(30) Foreign Application Priority Data

Mar. 11, 2015 (JP) .................................. 2015-048332

(51) Int. Cl.
*A61B 17/22* (2006.01)
*A61B 17/3207* (2006.01)
(Continued)

(52) U.S. Cl.
CPC ............. *A61B 17/320758* (2013.01); *A61B 17/22031* (2013.01); *A61B 17/3207* (2013.01);
(Continued)

(58) Field of Classification Search
CPC ...... A61B 17/22031; A61B 17/320758; A61B 2090/0811; A61B 2090/3966;
(Continued)

(56) References Cited

U.S. PATENT DOCUMENTS 3,732,858 A * 5/1973 Banko .............. A61B 17/32002
600/566
4,111,208 A * 9/1978 Leuenberger ...... A61B 17/1624
606/80

(Continued)

FOREIGN PATENT DOCUMENTS

| JP | 2003-079719 A | 3/2003 |
| JP | 2011-518618 A | 6/2011 |
| WO | WO 2006-121970 A2 | 11/2006 |

OTHER PUBLICATIONS

International Search Report (PCT/ISA/210) dated May 24, 2016, by the Japanese Patent Office as the International Searching Authority for International Application No. PCT/JP2016/057547.
(Continued)

*Primary Examiner* — Jing Rui Ou
(74) *Attorney, Agent, or Firm* — Buchanan Ingersoll & Rooney PC (57) ABSTRACT

A foreign object removal device is disclosed, which includes a protective sheath, and a device main body, which is disposed in a lumen of the protective sheath, can protrude from a distal end opening of the protective sheath communicating with the lumen and is rotatable relative to the protective sheath. The device main body includes, at a distal end portion protruding from the distal end opening, a screw which rotates integrally with the device main body and in which a flat plate is twisted, and side edges of the flat plate are formed in a spiral shape.

17 Claims, 6 Drawing Sheets

(51) Int. Cl.
*A61B 17/00* (2006.01)
*A61B 90/00* (2016.01)

(52) U.S. Cl.
CPC ............... *A61B 2017/00685* (2013.01); *A61B 2017/22035* (2013.01); *A61B 2017/22078* (2013.01); *A61B 2017/22094* (2013.01); *A61B 2090/0811* (2016.02); *A61B 2090/3966* (2016.02)

(58) Field of Classification Search
CPC ........... A61B 2017/00685; A61B 2017/22035; A61B 2017/22078; A61B 2017/22094; A61B 17/3207
See application file for complete search history.

(56) References Cited

U.S. PATENT DOCUMENTS

| | | | | |
|---|---|---|---|---|
| 4,710,075 | A * | 12/1987 | Davison | A61B 17/16 33/512 |
| 4,830,000 | A * | 5/1989 | Shutt | A61B 17/1615 408/207 |
| 5,423,824 | A * | 6/1995 | Akerfeldt | A61B 10/025 600/567 |
| 5,685,673 | A * | 11/1997 | Jarvis | B23B 51/02 408/230 |
| 6,045,566 | A | 4/2000 | Pagedas | |
| 6,267,542 | B1 * | 7/2001 | Salmon | B23B 51/02 408/223 |
| 7,806,871 | B2 | 10/2010 | Li et al. | |
| 7,988,389 | B2 * | 8/2011 | Miebach | B23B 51/02 408/211 |
| 8,517,994 | B2 | 8/2013 | Li et al. | |
| 2002/0058956 | A1 * | 5/2002 | Honeycutt | A61B 17/320758 606/159 |
| 2002/0151918 | A1 * | 10/2002 | Lafontaine | A61B 17/3207 606/159 |
| 2006/0015110 | A1 * | 1/2006 | Pepper | A61B 17/1615 606/80 |
| 2006/0253069 | A1 | 11/2006 | Li et al. | |
| 2007/0293867 | A1 * | 12/2007 | Anitua | A61B 17/1615 606/80 |
| 2009/0270888 | A1 * | 10/2009 | Patel | A61B 17/320758 606/159 |
| 2011/0021976 | A1 | 1/2011 | Li et al. | |
| 2012/0004661 | A1 * | 1/2012 | Leppelmeier | A61B 17/1615 606/80 |
| 2012/0041307 | A1 | 2/2012 | Patel et al. | |
| 2012/0209112 | A2 | 8/2012 | Patel et al. | |
| 2013/0138128 | A1 | 5/2013 | Patel et al. | |
| 2013/0338570 | A1 | 12/2013 | Li et al. | |
| 2014/0276840 | A1 | 9/2014 | Richter et al. | |

OTHER PUBLICATIONS

Written Opinion (PCT/ISA/237) dated May 24, 2016, by the Japanese Patent Office as the International Searching Authority for International Application No. PCT/JP2016/057547.

English language translation of the International Search Report and Written Opinion of the International Searching Authority (Forms PCT/ISA/237 and PCT/ISA/210) dated May 5, 2016, by the Japanese Patent Office in corresponding International Application No. PCT/JP2016/057547. (6 pages).

Office Action (Notice of Reasons for Refusal) dated Dec. 10, 2019, by the Japanese Patent Office in corresponding Japanese Patent Application No. 2017-505391 (6 pages including partial English translation).

\* cited by examiner

FOREIGN OBJECT REMOVAL DEVICE

CROSS-REFERENCES TO RELATED APPLICATIONS

This application is a continuation of International Application No. PCT/JP2016/057547 filed on Mar. 10, 2016, which claims priority to Japanese Application No. 2015-048332 filed on Mar. 11, 2015, the entire contents of which are incorporated herein by reference.

TECHNICAL FIELD

The present disclosure relates to a foreign object removal device, which removes foreign objects in living organs.

BACKGROUND DISCUSSION

In the blood vessels (living organs) such as arteries, occlusion or stenosis may occur due to the occurrence of atheroma (atheromatosis) or thrombus as foreign object. For such lesions, treatments can be performed to remove foreign objects by an interventional procedure using a foreign object removal device. As to the foreign object removal device, for example, a catheter system (so-called atherectomy device) which cuts an atheroma in a blood vessel as disclosed in JP-T-2011-518618.

SUMMARY

The disclosure has been made in relation to a procedure for removing foreign objects in a living organ as described above, and can include a foreign object removal device which allows the intervention procedure to be more preferably performed, by making it possible to recover a large amount of a foreign object in a short time with a simple configuration.

In accordance with an exemplary embodiment, a foreign object removal device is disclosed, which includes a protective sheath; and an elongated body which is disposed in a lumen of the protective sheath, can protrude from a distal end opening of the protective sheath communicating with the lumen, and is rotatable relative to the protective sheath, in which a screw which rotates integrally with the elongated body and has a twisted shape of a flat plate is provided at a distal end portion of the elongated body.

According to this configuration, the foreign object removal device can recover a large amount of a foreign object in a short time with a simple configuration in which a screw having a shape in which a flat plate is twisted is provided at the distal end portion of the elongated body. That is, the screw can allow the foreign object to smoothly flow by the inner twisted surface, while collapsing foreign objects in the living organ by side edges and distal end edges of the flat plate. Further, since the flow path formed by the twisted surface of the flat plate has a large cross-sectional area of the flow path and is smoothly formed, the flow path can allow a large amount of a foreign object to flow from the distal end of the screw to the proximal end side and to be guided to a lumen of the protective sheath. Therefore, the operator can more satisfactorily perform the intervention procedure. Here, the flat plate can be a sheet-like member having a flat or smooth surface and a thin thickness.

In accordance with an exemplary embodiment, it is preferable that a recess in which the vicinity of a rotation center of the screw is recessed in the proximal end direction be provided at the distal end of the screw.

In this way, by providing the recess, the screw can efficiently collapse the foreign object in the living organ by the portion protruding in the distal end direction on the radially outer side of the recess at the time of rotation.

Further, a maximum protrusion amount of the screw protruding from the distal end opening at the time of rotation of the screw may be set to be shorter than an interval until a phase is shifted by 180° from a distal end point connected to a distal end edge along a rotational direction of the screw, on the side edge which forms a radially outer edge portion of the screw.

As a result, since the foreign object removal device makes the screw shortly protrude from the protective sheath, after collapsing the foreign object by the rotation of the screw, foreign object can be immediately guided to the lumen of the protective sheath. Therefore, foreign object can be more efficiently recovered.

Further, a proximal end portion of the protective sheath and a proximal end portion of the elongated body are connected to each other so as to be movable relative to each other, and an adjusting mechanism capable of adjusting a protrusion amount of the screw may be provided at an interlock portion between the proximal end portion of the protective sheath and the proximal end portion of the elongated body.

In accordance with an exemplary embodiment, by providing the adjusting mechanism capable of adjusting the protrusion amount of the screw, the operator can easily set the maximum protrusion amount of the screw by manipulating the proximal end portion at the time of the procedure.

Furthermore, it can be preferable that a minimum protrusion amount of the screw protruding from the distal end opening at the time of rotation of the screw be set to be longer than an interval until a phase is shifted by 90° from the distal end point along the rotational direction of the screw on the side edge.

In this way, since the minimum protrusion amount of the screw is set to be longer than the interval until the phase is shifted by 90° from the distal end point along the rotational direction of the screw, the foreign object removal device can satisfactorily collapse the foreign object by the protruded screw.

Furthermore, it can be preferable that a length of a portion of the screw housed in the lumen from the distal end opening at the time of the rotation of the screw be longer than the interval until the phase is shifted by 180° from the distal end point along the rotational direction of the screw.

In accordance with an exemplary embodiment, since a length of a portion of the screw housed in the lumen from the distal end opening is longer than the interval until the phase is shifted by 180° from the distal end point along the rotational direction of the screw, the flow can be guided so that the foreign object flowing in the lumen is directed to the proximal end direction. As a result, the foreign object can be efficiently recovered in the lumen.

Further, a foreign object removal device according to another aspect of the disclosure can include a shaft capable of being inserted into a living body lumen and a screw, which is provided at a distal end portion of the shaft, rotates integrally with the shaft, and has a shape in which a flat plate is twisted.

According to this, the foreign object removal device of the disclosure can collapse a large amount of the foreign object in the living body lumen by a simple configuration in which a screw having a shape in which a flat plate is twisted at the distal end portion of the shaft is provided. Further, the screw allows the foreign object to smoothly flow by the inner twisted surface, while collapsing the foreign object in living organs by side edges or distal end edges of the flat plate. Therefore, the foreign object removal device of the disclosure can more satisfactorily perform the intervention procedure, in combination with another device that recovers the foreign object by suction or the like.

According to the disclosure, the foreign object removal device can satisfactorily perform the intervention procedure, making it possible to recover a large amount of the foreign object in a short time with a simple configuration.

In accordance with an exemplary embodiment, a method is disclosed for removing a foreign object from a living body, the method comprising: inserting a foreign removal object device into a blood vessel of a patient, the foreign removal object device including a protective sheath, an elongated body which is disposed in a lumen of the protective sheath, the elongated body configured to protrude from a distal end opening of the protective sheath communicating with the lumen, and is rotatable relative to the protective sheath, and a screw having a twisted shape of a flat pate and arranged at a distal end portion of the elongated body, and wherein the screw is configured to rotate integrally with the elongated body; guiding the foreign object removal device to an atheroma of a lesion in the blood vessel the patient; and crushing the atheroma by rotating and advancing the screw forward into the atheroma.

DETAILED DESCRIPTION

Preferred embodiments of the foreign object removal device according to the disclosure will be described below in detail with reference to the accompanying drawings.

The foreign object removal device 10 is a medical device, which can be used in an intervention procedure to remove foreign objects in living organs. Hereinafter, an atherectomy device for recovering foreign object such as atheroma or thrombus deposited on the endothelium of blood vessels (living organs) will be described in detail. For example, atheroma includes lipids such as cholesterol or neutral fat, lymphocytes, cells containing calcium or various fibrous connective tissues (macrophages). The foreign object removal device 10 is also applicable to various living organs (bile duct, trachea, esophagus, urethra, nasal cavity, and other organs) in addition to blood vessels, and the foreign object removal device 10 is applicable as, for example, equipment which recovers foreign objects such as pus or tumor in a living organ.

Figure 1:
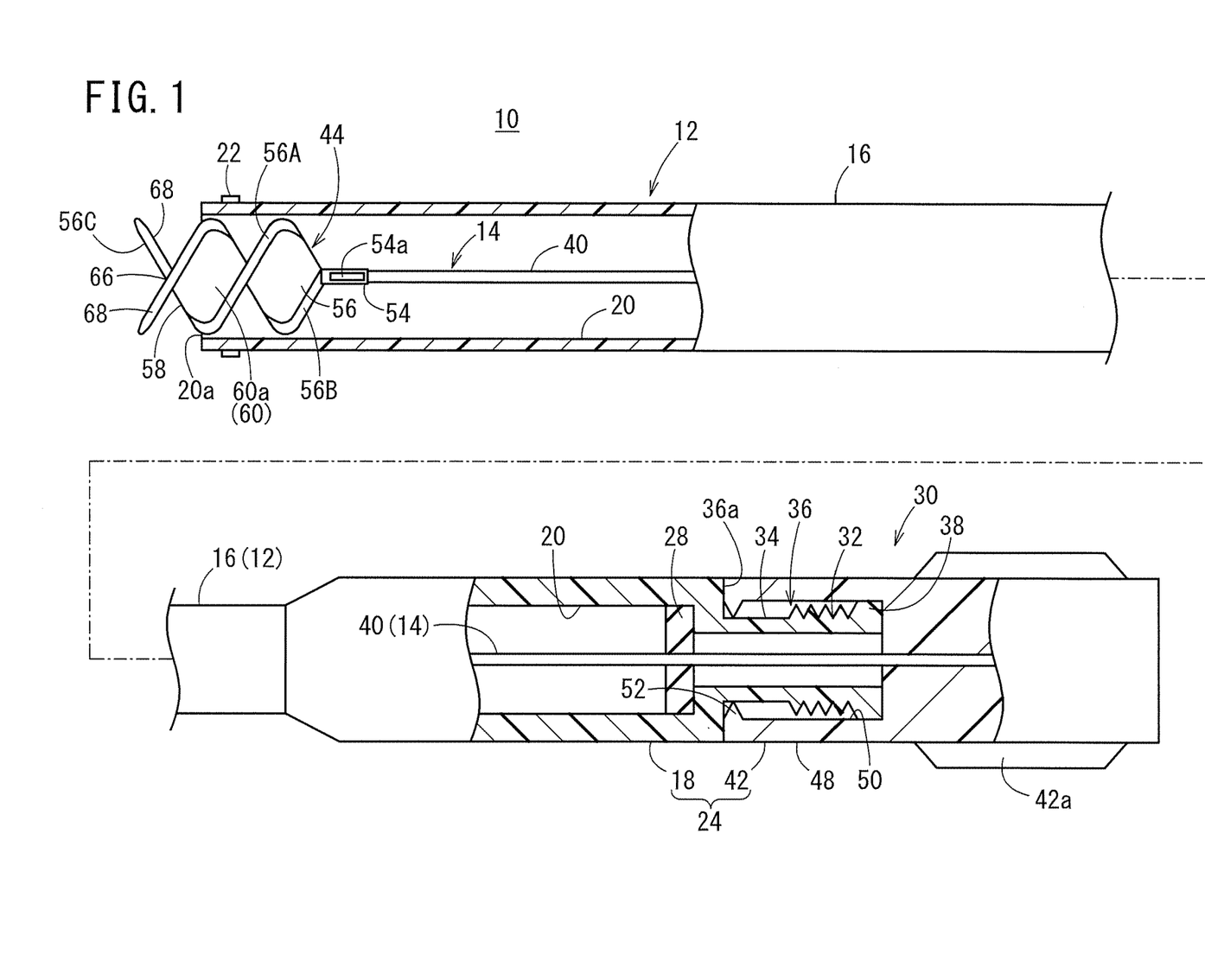
FIG. 1 is a partial side sectional view illustrating an overall configuration of a foreign object removal device according to an embodiment of the disclosure.

As illustrated in FIG. 1, the foreign object removal device 10 according to the present embodiment can include a tubular protective sheath 12, and a device main body 14 (elongated body) housed inside the protective sheath 12.

The protective sheath 12 has a function which protects the blood vessel (or the device main body 14) when delivering the device main body 14 to the lesion and captures the atheroma inside at the time of treatment of the device main body 14. Inside the protective sheath 12, a hollow portion 20 (lumen) which houses the device main body 14 is provided along the axial direction of the protective sheath 12. The protective sheath 12 can include a tube 16 elongated in the axial direction, and a sheath-side hub 18 connected to the proximal end portion of the tube 16.

In accordance with an exemplary embodiment, the tube 16 is thinner than the inner diameter of the blood vessel to be treated, and has a length reachable to the lesion. A distal end opening 20a communicating with the hollow portion 20 is formed at the distal end of the tube 16. In accordance with an exemplary embodiment, the inner diameters of the hollow portion 20 and the distal end opening 20a are set to a size corresponding to an outer diameter of a screw 44 of the device main body 14 which will be described later. Although not illustrated, in the tube 16, in addition to the hollow portion 20, a guide wire lumen for inserting a guide wire, which guides the foreign object removal device 10 may be arranged side by side. Alternatively, the guide wire may pass through the hollow portion 20.

In accordance with an exemplary embodiment, it can be preferable that the tube 16 has pliability (flexibility) capable of easily following meandering blood vessels, and has rigidity capable of housing the device main body 14 without bending. For example, as a material forming the tube 16, a polyolefin (for example, polyethylene, polypropylene, polybutene, ethylene-propylene copolymer, ethylene-vinyl acetate copolymer, ionomer, or a mixture of two or more thereof), a polymer material such as polyvinyl chloride, polyamide, polyamide elastomer, polyester, polyester elastomer, polyurethane, polyurethane elastomer, polyimide, and fluororesin, or a mixture thereof, or the aforementioned two or more polymer materials may be adopted. The tube 16 may be a multilayered tube formed by laminating a plurality of these materials. Further, in the vicinity of the distal end opening 20a of the tube 16, a contrast marker 22 recognizable under fluoroscopic vision may be provided.

In accordance with an exemplary embodiment, the sheath-side hub 18 is made of a harder material than the tube 16, and constitutes a part of an operation unit 24 to be grasped and operated by an operator (user). The hollow portion 20 penetrates the inside of the sheath-side hub 18. A valve body 28 which prevents the outflow of blood is housed in the hollow portion 20 in the sheath-side hub 18. One side of an adjusting mechanism 30 which adjusts the axial position of the device main body 14 is provided at the proximal end of the sheath-side hub 18. Further, the sheath-side hub 18 may have a side port on the distal end side of the valve body 28. Therefore, the interior of the protective sheath 12 can be easily primed with a saline solution or the like.

For example, the adjusting mechanism 30 on the side of the sheath-side hub 18 is a guide cylindrical portion 36 which has a male screw portion 32 formed in a spiral shape on the outer circumferential surface on the proximal end side in the axial direction, and a smooth portion 34 which is continuous with the distal end side of the male screw portion 32 and formed on the smooth outer circumferential surface in a sectional view. In this case, the male screw portion 32 screws the device main body 14 (the protrusion 52 of the main body-side hub 42) at the time of delivery of the protective sheath 12. Meanwhile, when the distal end of the protective sheath 12 reaches the lesion, and the operator releases the protrusion 52 of the main body-side hub 42 from the male screw portion 32, the smooth portion 34 places the device main body 14 in a freely rotatable manner. In accordance with an exemplary embodiment, the distal end of the smooth portion 34 is formed at a step 36a which interlocks the guide cylindrical portion 36 and the gripping portion of the sheath-side hub 18. A restriction unit 38 which restricts disengagement of the main body-side hub 42 may be provided at the proximal end of the male screw portion 32.

In accordance with an exemplary embodiment, the device main body 14 of the foreign object removal device 10 has a shaft 40 elongated in the axial direction, and a main body-side hub 42 connected to the proximal end portion of the shaft 40. Further, a screw 44 capable of entering and exiting the distal end opening 20a of the protective sheath 12 is provided in the distal end portion of the shaft 40. The device main body 14 can also be a foreign object removal device that removes foreign objects either independently or in cooperation with another device, without using the protective sheath 12.

In accordance with an exemplary embodiment, the shaft 40 is freely slidable in the axial direction with respect to the protective sheath 12 and rotatable around the axial center, and is inserted into the hollow portion 20 of the protective sheath 12. The shaft 40 is a solid rod member, and has an overall length corresponding to the axial length of the protective sheath 12, and an outer diameter sufficiently thinner than the hollow portion 20.

Although the material constituting the shaft 40 is not particularly limited, a resin material or a metal material harder than the tube 16 is preferable in order to transmit the rotational force of the main body-side hub 42 to the screw 44. Examples of the metal material include pseudoelastic alloys (including superelastic alloys) such as Ni—Ti alloys, shape memory alloys, stainless steel (for example, all kinds of SUS such as SUS304, SUS303, SUS316, SUS316L, SUS316J1, SUS316J1L, SUS405, SUS430, SUS434, SUS444, SUS429, SUS430F, and SUS302), cobalt-based alloys, noble metals such as gold and platinum, tungsten-based alloys, and carbon-based materials (including piano wires).

The main body-side hub 42 is disposed near the proximal end of the sheath-side hub 18, and the main body-side hub 42 and the sheath-side hub 18 constitute the operation unit 24 which the operator grasps and operates. Like the sheath-side hub 18, the main body-side hub 42 is made of a hard material, and firmly interlocks and holds the shaft 40 extending through the hollow portion 20 of the protective sheath 12 and in the proximal end direction.

The distal end side of the main body-side hub 42 and the proximal end side of the sheath-side hub 18 form the adjusting mechanism 30. In accordance with an exemplary embodiment, on the distal end side of the main body-side hub 42, a housing cylindrical portion 48 having a housing hole portion 50 capable of housing the guide cylindrical portion 36 of the sheath-side hub 18 is formed. One or more protrusions 52 protruding inward in the radial direction are provided on the inner surface on the distal end side of the housing cylindrical portion 48. The protrusion 52 is screwed with the male screw portion 32 of the sheath-side hub 18, while being disposed to be relatively rotatable with respect to the smooth portion 34.

The adjusting mechanism 30 is configured so that the distal end of the screw 44 is positioned in the hollow portion 20 in a state in which the protrusion 52 is disposed in the male screw portion 32, and the screw 44 protrudes from the distal end opening 20a in a state in which the protrusion 52 is disposed in the smooth portion 34. In a state in which the device main body 14 is rotatable, the shaft 40 rotatably comes into contact with the valve body 28 to stabilize the axial position of the device main body 14. Further, when the distal end of the housing cylindrical portion 48 comes into contact with the step 36a under the operation of the operator, advancement of the device main body 14 is restricted, and the screw 44 protrudes from the distal end opening 20a at a predetermined protrusion amount (for example, a maximum protrusion amount Xmax to be described later).

In accordance with an exemplary embodiment, the protrusion 52 strikes the restriction unit 38 in the retraction in the proximal end direction, thereby restricting further retraction. As a result, detachment between the sheath-side hub 18 (protective sheath 12) and the main body-side hub 42 (device main body 14) can be prevented. The operation unit 24 may be provided with a rotation preventing mechanism (not illustrated) that restricts the rotation of the main body-side hub 42 when the main body-side hub 42 is disposed at a predetermined axial position of the sheath-side hub 18.

The relative rotation of the main body-side hub 42 with respect to the sheath-side hub 18 is transmitted to the shaft 40 to rotate the screw 44 of the distal end side. A rib 42a (auxiliary portion) which assists the rotational operation of the device main body 14 performed by the operator may be formed on the outer circumferential surface of the main body-side hub 42. Further, the main body-side hub 42 may be connected to an actuator (rotational driving mechanism) (not illustrated), and a rotational force may be given thereto.

Figure 2A:
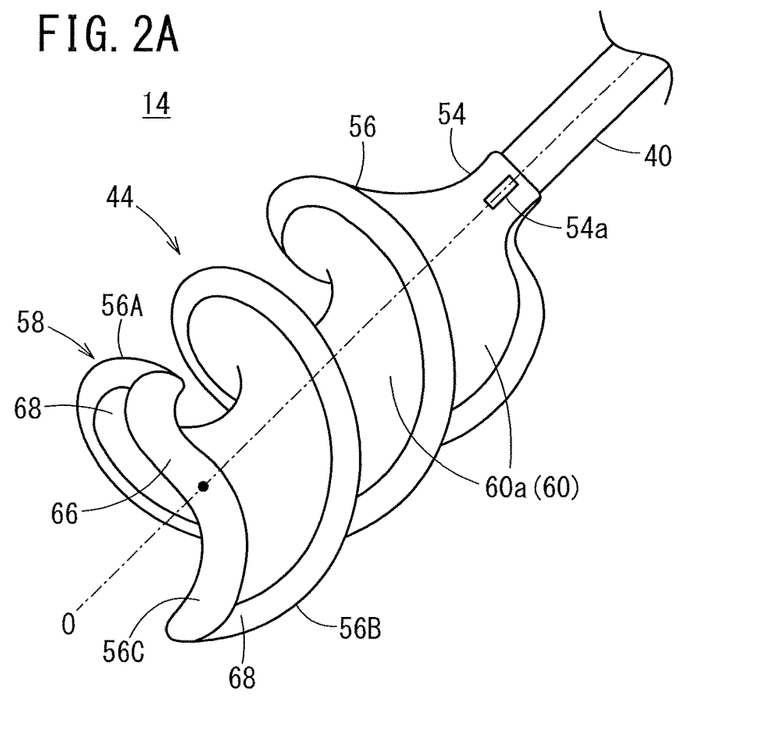
FIG. 2A is a perspective view of a screw.
Figure 2B:
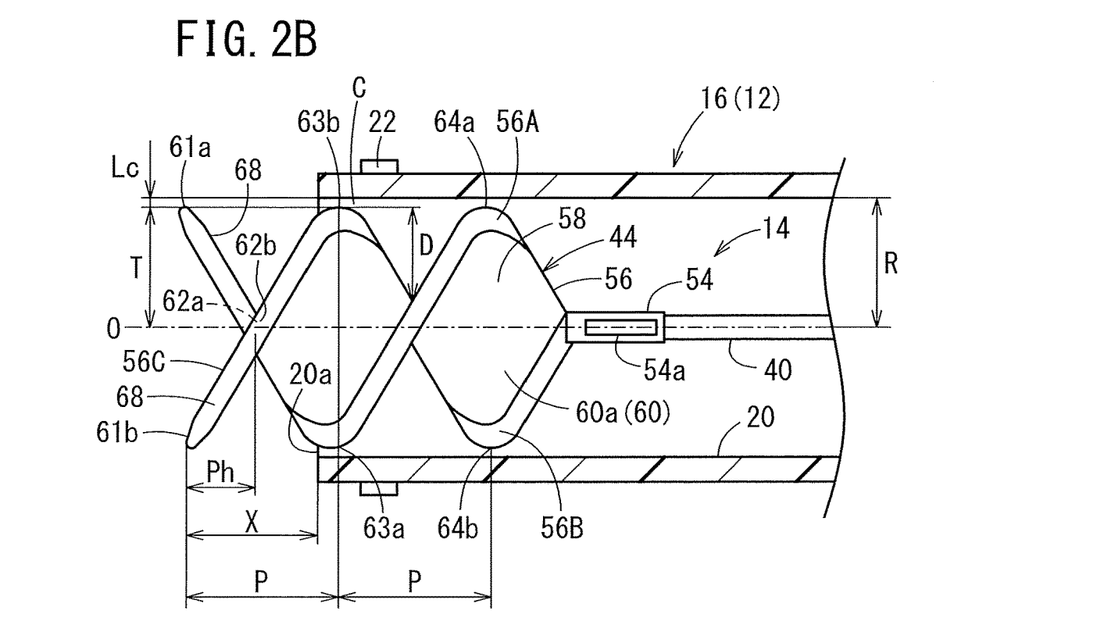
FIG. 2B is a side view illustrating a relation between a protective sheath and the screw.

The screw 44 provided at the distal end of the shaft 40 has a function of inducing the atheroma in the blood vessel to the hollow portion 20 of the protective sheath 12, while collapsing (crushing) the atheroma by rotation. As illustrated in FIGS. 2A and 2B, the screw 44 has a tubular interlock portion 54, which covers the distal end of the shaft 40, a rotation recovery unit 58 having a twisted shape which is connected to the interlock portion 54 and has a flat plate 56 protruding in the distal end direction.

In accordance with an exemplary embodiment, the interlock portion 54 is fixed to the shaft 40 by an appropriate fixing means such as welding or adhesion to integrate the shaft 40 and the screw 44. In accordance with an exemplary embodiment, a contrast marker 54a having a radiation contrast property is attached to the interlock portion 54. The contrast marker 54a may be provided on a part of circumferential direction so that the rotation of the screw 44 can be checked, and the position thereof may vary with the rotation. When the adjusting mechanism 30 is not included, the foreign object removal device 10 can recognize the amount of protrusion of the screw 44, by the relative position between the contrast marker 22 of the protective sheath 12 and the contrast marker 54a of the device main body 14. Further, by forming the screw 44 from a material having radiation contrast properties, the rotation may be checked.

In accordance with an exemplary embodiment, the rotation recovery unit 58 is a part that protrudes from the protective sheath 12 and directly takes the atheroma into the hollow portion 20 of the protective sheath 12. The rotation recovery unit 58 (the flat plate 56) has a pair of side edges 56A and 56B that form the radially outer edge portion of the screw 44. The pair of side edges 56A and 56B has a twisted shape wound in a spiral shape. A twisted surface 60 forming both surfaces of the flat plate 56 is present between the pair of side edges 56A and 56B, and the twisted surface 60 forms a spiral flow path 60a through which the atheroma flows. In accordance with an exemplary embodiment, the twisted surface 60 is continuous with a smooth surface without being locally raised or depressed because there is no columnar core at the rotation center. Further, the thickness of the flat plate 56 can be relatively thinner, and thus, the flow path 60a has a large cross-sectional area of the flow path.

In accordance with an exemplary embodiment, the side edges 56A and 56B form a double spiral that twists, while sandwiching the rotation center axis O of the screw 44, and maintains opposite positions (positions with the different phases of) 180°. In the side view illustrated in FIG. 2B, the pair of side edges 56A and 56B has distal end points 61a and 61b connected to the distal end edge 56C of the flat plate 56 at the most distal side. The distal end edge 56C of the screw 44 is a portion that forms the edge portion on the distal end side of the flat plate 56 from the rotation center axis O to the pair of side edges 56A and 56B.

Further, the screw 44 is twisted from the distal end points 61a and 61b in the proximal end direction, the phases of the side edges 56A and 56B change by 90° at the side points 62a and 62b, and the phases change by 180° to the distal end points 61a and 61b at the side points 63a and 63b. Furthermore, the phases of the side edges 56A and 56B change by 180° with respect to the side points 63a and 63b at the side points 64a and 64b. In accordance with an exemplary embodiment, the side edges 56A and 56B make one revolution in the range from the distal end points 61a and 61b to the side points 64a and 64b. The flat plate 56 is formed to smoothly converge from the side points 64a and 64b toward the interlock portion 54.

FIG. 2B illustrates the side surface in which the top portion of the waveform formed by the side edges 56A and 56B of the flat plate 56 is most visible. In the side view, the screw 44 forms waveforms symmetrical to the top and bottom of the rotation center axis O. The distal end point 61a, the side points 63a and 64a, the distal end point 61b, and the side points 63b and 64b are located at the top portions of the waveforms which protrude from the rotation center axis O of the rotation recovery unit 58 in directions opposite to each other.

A pitch (interval P) of the same dimension is set between the distal end point 61a and the side point 63b (or the distal end point 61b and the side point 63a), and between the side point 63b and the side point 64a (or the side point 63a and the side point 64b). That is, the rotation recovery unit 58 has a uniform degree of twisting. As a result, since the volume of the flow path 60a can be made constant, the rotation recovery unit 58 suppresses stagnation of the atheroma to make the atheroma smoothly flow in the proximal end direction. Further, each interval P may be formed to spread toward the proximal end direction.

Each interval P is not particularly limited, but the interval may be approximately the same as the height T (the radius of the rotation recovery unit 58) from the rotation center axis O of the screw 44 to the side edges 56A and 56B, or is approximately slightly longer than the height T (for example, the length not more than twice the height T). When the interval P is extremely long, the atheroma passing through the flow path 60a can easily leak to the outside of the screw 44. In accordance with an exemplary embodiment, when the interval P is extremely short, the flow path 60a through which the atheroma flows is narrowed, and the efficiency of the recovery decreases.

The side edges 56A and 56B of the rotation recovery unit 58 are formed to have a height T so as to be close to the inner surface of the protective sheath 12, and sufficiently narrow the length Lc of the clearance C between the screw 44 and the protective sheath 12. In accordance with an exemplary embodiment, the length Lc of the clearance C may be in the range of 2.5% to 7.5% of the inner diameter of the protective sheath 12, based on the experimental results to be described later. Since the foreign object removal device 10 has the clearance C, the relative movement and the relative rotation of the screw 44 in the axial direction to the protective sheath 12 become relatively smooth.

Further, the depth D (the dimension from the side edges 56A and 56B to the vicinity of the rotation center axis O on the radially inner side) of the flow path 60a formed by the rotation recovery unit 58 is preferably set to ⅓ or higher of the diameter (2T) of the rotation recovery unit 58. In accordance with an exemplary embodiment, in the screw 44, the thickness of the flat plate 56 is set to be sufficiently thin. As a result, since the flow path 60a of the rotation recovery unit 58 is sufficiently large, the removal amount (recovery amount) of the atheroma is considerably greater than that of a case in which the depth D is shallower than ⅓ of the diameter of the rotation recovery unit 58.

As illustrated in FIG. 2B, the rotation recovery unit 58 according to the present embodiment has a recess 66 configured such that the distal end edge 56C of the flat plate 56 is recessed in a V-shape (or U-shape) in the direction of the proximal end of the device main body 14. Due to the recess 66, the distal end edge 56C presents fins 68 in which the distal end points 61a and 61b side protrude toward the distal end direction from the central portion.

In accordance with an exemplary embodiment, the screw 44 is housed in the hollow portion 20 of the protective sheath 12 at the time of delivering the foreign object removal device 10. Further, in order to recover (remove) the atheroma, the operator makes the distal end side of the screw 44 protrudes from the distal end opening 20a of the protective sheath 12 at the position close to the lesion. The protrusion amount X of the rotation recovery unit 58 with respect to the distal end opening 20a of the protective sheath 12 can be adjusted by the adjusting mechanism 30 illustrated in FIG. 1.

Here, the foreign object removal device 10 is preferable to make the distal end of the rotation recovery unit 58 slightly protrude when recovering the atheroma. Specifically, as illustrated in FIG. 2B, the maximum protrusion amount Xmax of the rotation recovery unit 58 is set to an amount in which the side points 63a and 63b located at the intermediate portion on the side edges 56A and 56B of the flat plate 56 do not come out of the distal end opening 20a. That is, the maximum protrusion amount Xmax of the rotation recovery unit 58 is set to be shorter than the interval P to the side points 63a and 63b in which the side edges 56A and 56B of the rotation recovery unit 58 change by 180° from the distal end points 61a and 61b along the rotational direction. In this way, since the maximum protrusion amount Xmax of the rotation recovery unit 58 is short, while collapsing the atheroma by the portion protruding from the protective sheath 12 of the rotation recovery unit 58, the collapsed atheroma can be made to directly flow into the hollow portion 20 from the distal end opening 20a of the protective sheath 12.

Further, when recovering the atheroma, the rotation recovery unit 58 preferably at least protrudes from the distal end opening 20a in the range from the distal end points 61a and 61b to the side points 62a and 62b. That is, the minimum protrusion amount Xmin of the rotation recovery unit 58 is set to be longer than the interval Ph from the distal end points 61a and 61b to the side points 62a and 62b that change by 90° in the rotational direction. In this manner, since the rotation recovery unit 58 protrudes to a greater extent than the side points 62a and 62b, the interference between the protective sheath 12 and the lesion can be suppressed and the rotation recovery unit 58 can be satisfactorily brought into contact with the lesion. That is, the protrusion amount X of the rotation recovery unit 58 is preferably set to satisfy the relation of Ph<X<P.

In accordance with an exemplary embodiment, a portion of the rotation recovery unit 58, which is housed in the hollow portion 20 from the distal end opening 20a at the time of rotation, is preferably longer than the interval P. In this way, in a case where the rotation recovery unit 58 is long, when the atheroma is recovered, the flow can be guided so that the atheroma which has flowed into the hollow portion 20 flows in the proximal end direction, rather than immediately flowing outward in the radial direction. Therefore, the atheroma is efficiently recovered in the hollow portion 20.

Returning to FIG. 1, in the adjusting mechanism 30, when the distal end side of the rotation recovery unit 58 protrudes from the distal end opening 20a of the protective sheath 12 just by the protrusion amount X, the distal end of the main body-side hub 42 and the sheath-side hub 18 come into contact with each other to restrict the further advancement. In addition to such a configuration, the foreign object removal device 10 may be configured such that the screw 44 protrudes in a larger amount than the interval P from the protective sheath 12, in order to recover atheroma close to the endothelium (side wall) side of the blood vessel.

In accordance with an exemplary embodiment, the material forming the screw 44 is not particularly limited as long as it has hardness capable of crushing and recovering atheroma, and an appropriate resin material or metal material can be applied. Examples of the resin material may include phenol resin, melamine resin, polyester resin, epoxy resin, polyethylene, polypropylene, ABS resin, AS resin, polyurethane, polyamide, polycarbonate, polybutadiene, polyvinyl chloride, and polyolefin such as ethylene-vinyl acetate copolymer. Further, as the metal material, the material mentioned for the constituent material of the shaft 40 can be applied. In accordance with an exemplary embodiment, the shaft 40 and the screw 44 may be integrally formed of the same material.

The foreign object removal device 10 according to the present embodiment is basically configured as described above. Next, the use method and effect thereof will be described with reference to FIGS. 3A to 3C. The foreign object removal device 10 is used when performing an intervention procedure on a patient with atherosclerosis.

In the foreign object removal device 10, the device main body 14 is disposed in the hollow portion 20 of the protective sheath 12, and the screw 44 is inserted into the blood vessel V by the operator in an unexposed state. That is, the adjusting mechanism 30 (see FIG. 1) of the foreign object removal device 10 sets the main body-side hub 42 at a position moved backward in the proximal end direction with respect to the sheath-side hub 18 when the male screw portion 32 screws the protrusion 52.

Figure 3A:
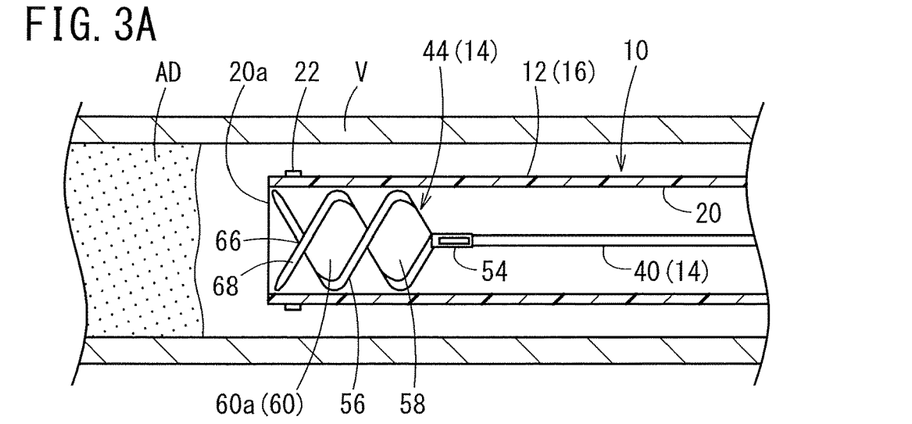
FIG. 3A is a first explanatory view illustrating an operation of the foreign object removal device.

The operator grasps the operation unit 24 (the sheath-side hub 18 and the main body-side hub 42) of the foreign object removal device 10 and delivers the distal end portion of the protective sheath 12 to the lesion AD (deposition position of atheroma A) in the blood vessel along a guide wire (not illustrated). At this time, since the device main body 14 is housed in the protective sheath 12, the foreign object removal device 10 can smoothly proceed inside the blood vessel V.

Figure 3B:
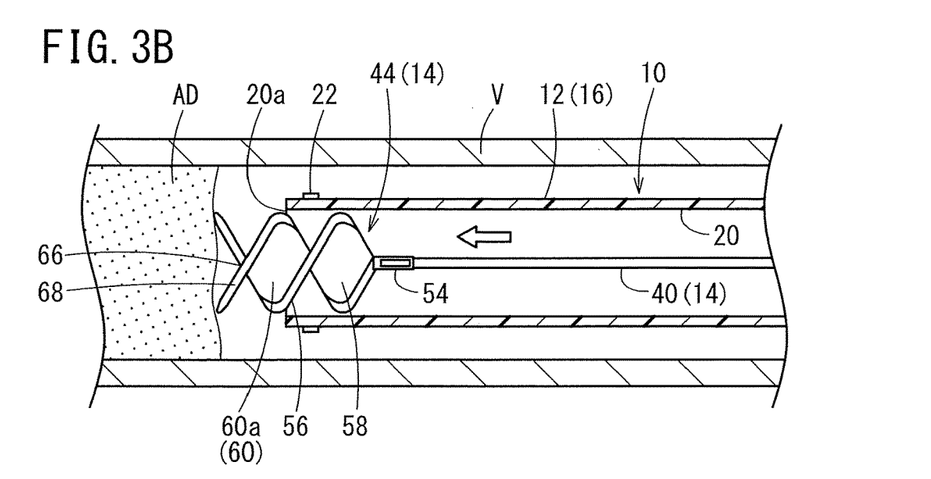
FIG. 3B is a second explanatory view illustrating an operation following the operation of FIG. 3A.

When the distal end of the foreign object removal device 10 reaches the lesion AD, the operator operates the main body-side hub 42 to advance in the distal direction with respect to the sheath-side hub 18. At the time of this operation, the main body-side hub 42 is rotated with respect to the sheath-side hub 18 to release screwing between the male screw portion 32 and the protrusion 52, and the protrusion 52 is made to advance to the smooth portion 34 (see FIG. 1), thereby adjusting the protrusion amount X of the screw 44. For example, when the distal end of the main body-side hub 42 is brought into contact with the step 36a, only a part (distal end side from the side points 62a and 62b) of the rotation recovery unit 58 protrudes from the distal end opening 20a of the protective sheath 12 as illustrated in FIG. 3B (see also FIG. 2B).

Figure 3C:
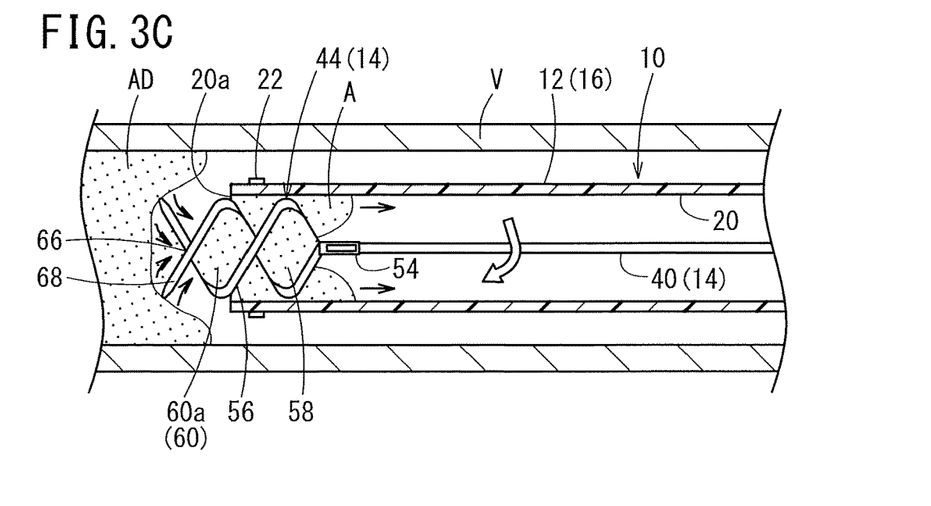
FIG. 3C is an explanatory view illustrating an operation following the operation of FIG. 3B.

After protrusion of the screw 44, the operator rotates the main body-side hub 42 with respect to the sheath-side hub 18. As a result, the rotational force of the main body-side hub 42 is transmitted to the screw 44 via the shaft 40, and the screw 44 rotates at the distal end of the protective sheath 12 as illustrated in FIG. 3C. The screw 44 is inserted into the atheroma A of the lesion AD and collapses the atheroma A by advancing while rotating. At this time, the fins 68 of the screw 44 promote crushing of the lesion AD.

The atheroma A collapsed by the rotation of the screw 44 is guided to the hollow portion 20 of the protective sheath 12 through the flow path 60a of the rotation recovery unit 58. In accordance with an exemplary embodiment, since the protrusion amount X of the screw 44 from the distal end opening 20a of the protective sheath 12 is short, the atheroma A more rapidly enters the protective sheath 12 toward the radially outer side of the screw 44. As a result, the foreign object removal device 10 suppresses diffusion of the atheroma A into the blood vessel V and satisfactorily recovers the atheroma A in the blood vessel V. After recovery of the atheroma A, the procedure is completed by extracting the foreign object removal device 10 from the blood vessel V.

In this way, the foreign object removal device 10 can recover a large amount of atheroma A in a short time with a simple configuration in which the screw 44 having a twisted shape of the flat plate 56 is provided at the distal end portion of the device main body 14. That is, the screw 44 allows the atheroma to smoothly flow by the twisted surface 60 of the flat plate 56, while collapsing the atheroma A by the side edges 56A and 56B and the distal end edge 56C of the flat plate 56. Since the flow path 60a formed by the twisted surface 60 has a large cross-sectional area of the flow path and is smoothly formed, a large amount of the atheroma A flows from the distal end of the screw 44 to the proximal end side and can be guided to the hollow portion 20 of the protective sheath 12. Therefore, the operator can more satisfactorily perform the intervention procedure.

In this case, by providing the recess 66, the screw 44 can efficiently collapse the atheroma A deposited in the blood vessel V, by the fins 68 that protrude in the distal direction on the radially outer side of the recess 66 at the time of rotation.

Further, the foreign object removal device 10 is not limited to the above embodiment, and various application examples or modified examples can be adopted. For example, the shape in which the flat plate 56 of the screw 44 is twisted is not limited to the aforementioned shape, and can be arbitrarily set. In accordance with an exemplary embodiment, the twisted amount of the side edges 56A and 56B may be not only one turn as in the present embodiment, but also a length of one turn or more, and may be a half turn. In short, as long as the portion of the screw 44 protruding from the protective sheath 12 is formed in a spiral shape, foreign object of the living organ can be satisfactorily guided into the protective sheath 12. Further, for example, the foreign object removal device 10 may be provided with a support frame, which supports the rotation of the screw 44, on the proximal end side of the screw 44 in the hollow portion 20 of the protective sheath 12.

Further, the structure of the adjusting mechanism 30 is not particularly limited, as long as it is possible to allow the screw 44 to appropriately protrude from the distal end opening 20a, while allowing the rotation of the screw 44. For example, since the adjusting mechanism 30 includes a rotatable portion (not illustrated) which is rotatable relative to the sheath-side hub 18, and the main body-side hub 42 is fitted to the rotatable portion with advancement, a torque device can be applied that sets the protrusion amount X of the screw 44 and freely rotates.

Further, as in the modified example illustrated in FIG. 4A, in the screw 44A, the recess 66 (see FIG. 2B) is not formed at the distal end edge 56C of the rotation recovery unit 58, and the distal end edge 56C may be linearly formed (hereinafter, also referred to as linear edge portion 70). Even when the linear edge portion 70 is formed in this manner, the rotation recovery unit 58 can collapse the atheroma by the linear edge portion 70 at the time of rotation. Further, the screw 44A can further simplify the manufacture of the rotation recovery unit 58.

Figure 4A:
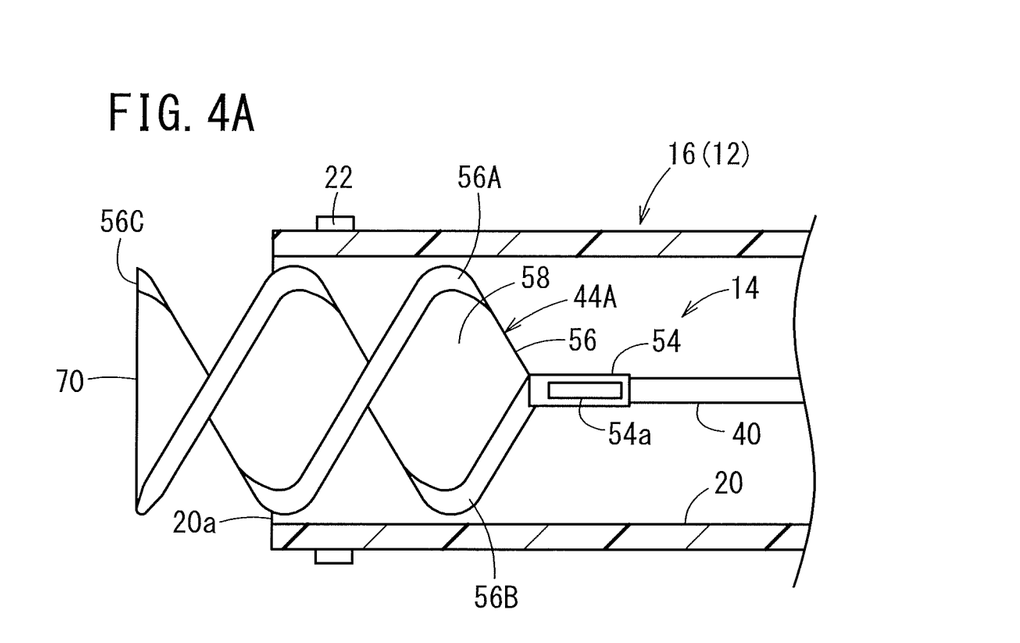
FIG. 4A is a side view illustrating a screw according to a modified example.
Figure 4B:
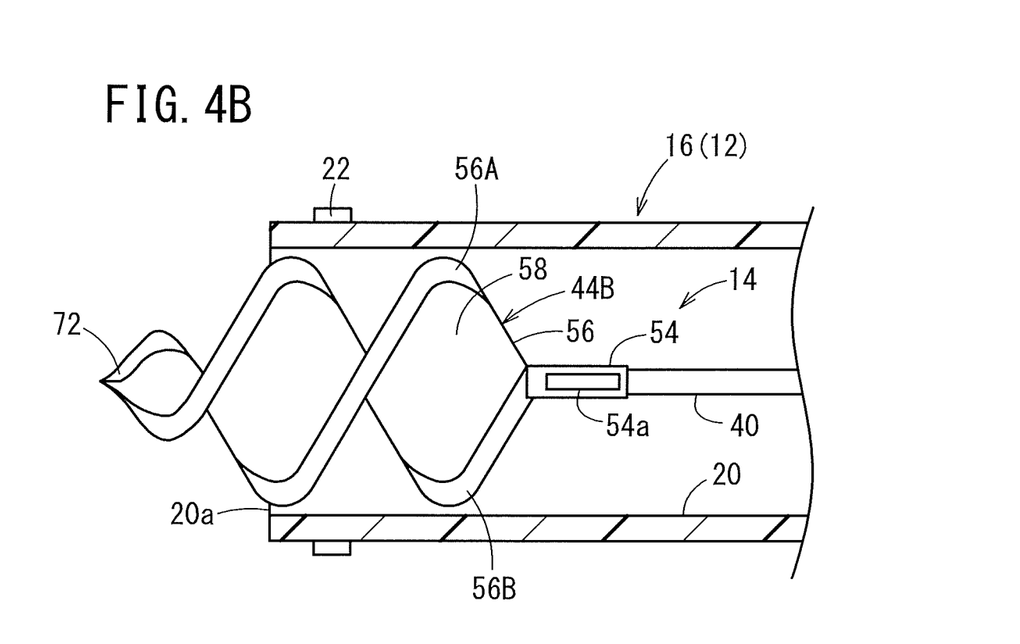
FIG. 4B is a side view illustrating a screw according to a reference example.

Further, as in the reference example illustrated in FIG. 4B, it is also considered that the screw 44B does not have the distal end edge 56C, and a sharply pointed portion 72 is formed by protrusion of the rotation center axis O side of the rotation recovery unit 58 in the distal end direction. However, when the rotation recovery unit 58 has the sharply pointed portion 72, the removal amount of foreign object can be greatly reduced as compared with the other screws 44 and 44A as in the experimental results described later.

The applicant of the disclosure conducted several experiments to check the difference in shape of the screw 44 and its recovery capability, on the foreign object removal device 10 according to the disclosure. The experimental results are illustrated in FIGS. 5A to 6C.

In a first exemplary embodiment, an experiment was conducted, which compares the recovery ability of the screw 44 having the recess 66 illustrated in FIG. 1, the screw 44A having the linear edge portion 70 illustrated in FIG. 4A, and the screw 44B having the sharply pointed portion 72 illustrated in FIG. 4B.

In the experiment, an agarose gel (agar) was formed in a three-dimensional shape as a foreign object model recovered by the foreign object removal device 10. Specifically, an agarose gel was placed as a foreign object model in the lumen of a tube having a diameter of 8.0 mm, and a partial region of the lumen of the tube was closed with an agarose gel. The foreign object removal device 10 in a state in which the screws 44, 44A and 44B protruded from the protective sheath 12 was inserted into the agarose gel from the distal end. In the inserted state, the agarose gel was recovered by rotating the screws 44, 44A, and 44B. Further, in accordance with the recovery speed, the foreign object removal device 10 was caused to enter the foreign object model and to reach a depth of 20 mm.

Figure 5A:
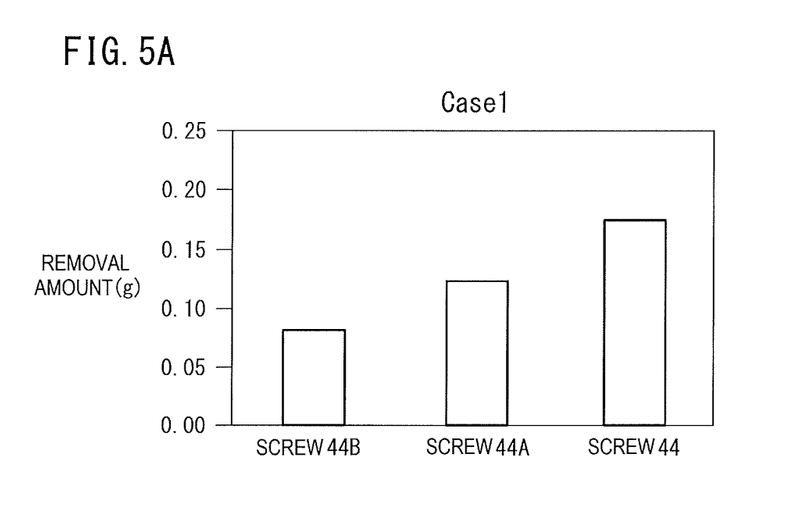
FIG. 5A is a graph comparing removal amounts of various screws to a foreign object model having an agarose concentration of 1.0 wt %.
Figure 5B:
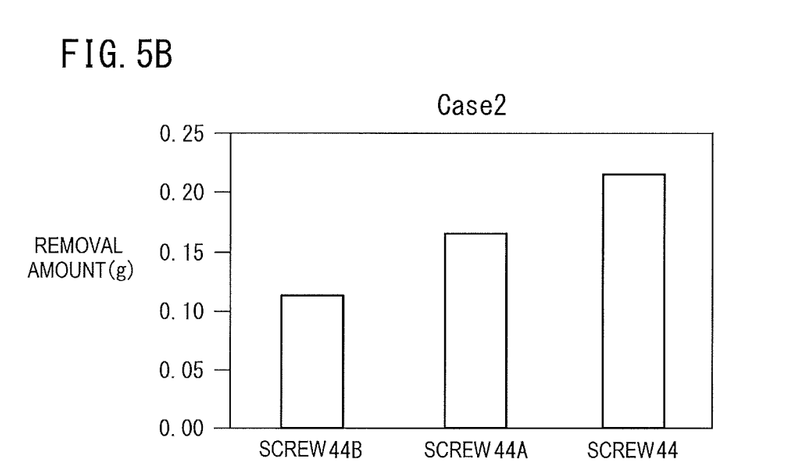
FIG. 5B is a graph comparing removal amounts of various screws with respect to a foreign object model having an agarose concentration of 4.0 wt %.

The removal amounts of agarose gel using the screws 44, 44A, and 44B at this time are illustrated in the graphs of FIGS. 5A and 5B. In the graphs of FIGS. 5A and 5B, a screw 44B having the sharply pointed portion 72, a screw 44A having a linear edge portion 70, and a screw 44 having a recess 66 are arranged in this order from the left to the right of the horizontal axis. The protective sheaths 12 having the same shape were used. Further, in the experiment, the protrusion amount X of the distal end of the screw 44 with respect to the distal end opening 20a of the protective sheath 12 was also set to the same length.

The graph illustrated in FIG. 5A is a case where a foreign object model of an agarose gel having an agarose concentration of 1.0 wt % was used (Case 1), and this foreign object model assumes an atheroma A formed soft in the blood vessel V. Meanwhile, the graph illustrated in FIG. 5B is a case where a foreign object model of agarose gel having an agarose concentration of 4.0 wt % was used (Case 2), and this foreign object model assumes an atheroma A hardened by advancing to some extent in the blood vessel V.

As illustrated in FIGS. 5A and 5B, in the experiment, the screw 44 having the recess 66 at the distal end recovered the largest amount of agarose gel. Subsequently, the removal amount of the agarose gel of the screw 44A having the linear edge portion 70 was large. In contrast, the removal amount of the agarose gel was small in the screw 44B having the sharply pointed portion 72. The reason for this is considered that the screw 44B can pierce the sharply pointed portion 72 into the agarose gel, but the effective volume for scraping off the agarose gel is small and the agarose gel is avoided beside the screw 44B. Meanwhile, it can be said that the screws 44 and 44A have a large effective volume and can easily scrape off the agarose gel. Further, the reason why the removal amount when the screw 44 has the recess 66 was the largest is presumed that the agarose gel is efficiently collapsed by the fin 68 on the outer side of the distal end of the screw 44 and is sent in the direction of the proximal end of the screw 44.

In accordance with an exemplary embodiment, the screw 44 with the recess 66 had the highest speed advancing inside the agarose gel (that is, recovery speed), and the screw 44A with the linear edge portion 70 was the second fastest. From the result of the first embodiment, it is preferable to make the foreign object removal device 10 have a shape within a range from a linear shape to a point where the central portion (rotation center axis O) is recessed in the proximal end direction, with respect to the distal end edge 56C of the screw 44.

Figure 6A:
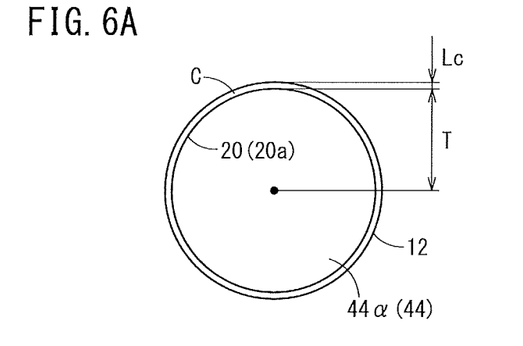
FIG. 6A is a schematic front view illustrating a screw with a gap of 2.5%.
Figure 6B:
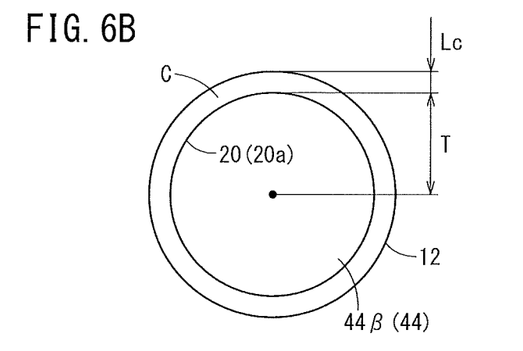
FIG. 6B is a schematic front view illustrating a screw with a gap of 8.5%.

In a second exemplary embodiment, the difference in recovery capability was checked by changing the inner diameter of the protective sheath 12 with respect to the outer diameter of the screw 44. Specifically, as illustrated in FIG. 6A, a screw 44α having an outer diameter of 95% with respect to the inner diameter of the hollow portion 20 of the protective sheath 12, and as illustrated in FIG. 6B, a screw 44β having an outer diameter of 83% with respect to the inner diameter of the hollow portion 20 of the protective sheath 12 were prepared. Conversely, in the screw 44α illustrated in FIG. 6A, when the axial centers of the screw 44α and the protective sheath 12 coincide with each other, a length Lc of the clearance C between the protective sheath 12 and the screw 44α is a length of 2.5% with respect to the inner diameter of the protective sheath 12. Further, in the screw 44β illustrated in FIG. 6B, when the axial centers of the screw 44β and the protective sheath 12 coincide with each other, a length Lc of the clearance C between the protective sheath 12 and the screw 44β is set as a length of 8.5% with respect to the inner diameter of the protective sheath 12. Further, the screw 44α illustrated in FIG. 6A has a clearance C of at least 9.75% between the protective sheath 12 and the screw 44α with respect to the cross-sectional area of the hollow portion 20 of the protective sheath 12. Further, the screw 44β illustrated in FIG. 6B has a clearance C of at least 31.11% between the protective sheath 12 and the screw 44β with respect to the cross-sectional area of the hollow portion 20 of the protective sheath 12.

Further, as in the first example, screws 44α and 44β were inserted into the foreign object model of the agarose gel from the distal end and rotated, and the removal amount of the agarose gel when reaching 20 mm was compared. The conditions of other experiments were also the same as in the first embodiment.

Figure 6C:
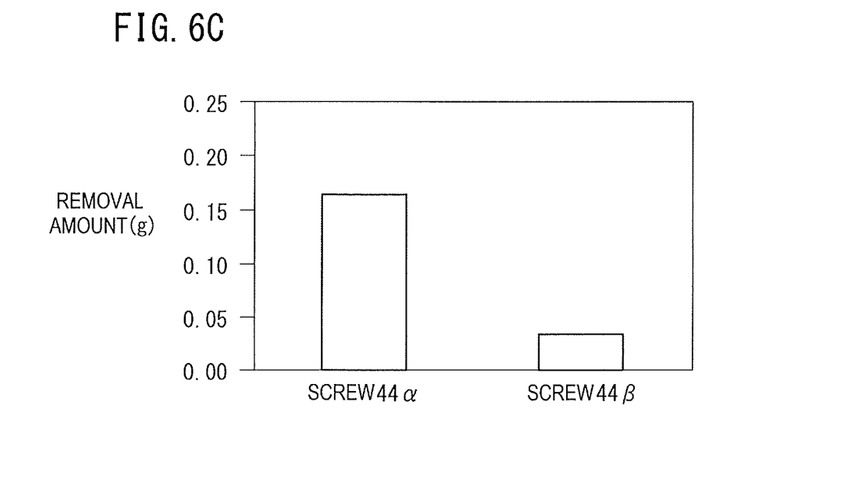
FIG. 6C is a graph comparing the removal amounts of screws between a screw with a gap of 2.5% and a screw with a gap of 8.5%.

As illustrated in FIG. 6C, in the experiment, the removal amount of the agarose gel in the screw 44α having the length Lc of the clearance C of 2.5% was larger than that in the screw 44β having the length Lc of the clearance C of 8.5%. The reason for this is considered that the screw 44α has more effective volume enough to scrape off the agarose gel. Further, since the screw 44α almost blocks the distal end opening 20a of the protective sheath 12, it is estimated that the agarose gel guided to the hollow portion 20 can smoothly flow in the proximal end direction.

From the result of the second embodiment, the clearance C between the protective sheath 12 and the screw 44 is required to be sufficiently small. For example, the length Lc is desired to be a ratio smaller than 8.5% with respect to the inner diameter of the hollow portion 20. More preferably, the length Lc of the clearance C between the protective sheath 12 and the screw 44 is within the range of 0.5% to 7.5% with respect to the inner diameter of the hollow portion 20. More preferably, the length Lc of the clearance C between the protective sheath 12 and the screw 44 is within a range of 1.0% to 5.0% with respect to the inner diameter of the hollow portion 20.

The detailed description above describes a foreign object removal device which removes foreign object in living organs. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A foreign object removal device comprising:
 a protective sheath;
 an elongated body which is disposed in a lumen of the protective sheath, the elongated body configured to protrude from a distal end opening of the protective sheath communicating with the lumen, and is rotatable relative to the protective sheath;
 a screw having a twisted shape of a flat plate and arranged at a distal end portion of the elongated body, and wherein the screw is configured to rotate integrally with the elongated body;
 a maximum protrusion amount of the screw protruding from the distal end opening of the protective sheath at a time of rotation of the screw being set to be less than an interval of the screw, the interval of the screw being a distance along a rotational center axis of the screw between a distal end point of the screw and a first side point of the screw with the first side point of the screw being shifted 180 degrees from the distal end point of the screw along a rotational direction of the screw; and
 wherein the distal end point is connected to a distal end edge, the distal end edge being a portion of the screw that forms an edge portion on a distal end side from the rotational center axis of the screw to a side edge of the screw, and wherein the side edge forms a radially outer edge portion of the screw.

2. The foreign object removal device according to claim 1, wherein a rotational center of the screw is recessed in a proximal end direction at a distal end of the screw.

3. The foreign object removal device according to claim 1, wherein a proximal end portion of the protective sheath and a proximal end portion of the elongated body are connected to each other so as to be movable relative to each other, and an adjusting mechanism configured to adjust a protrusion amount of the screw is provided at an interlock portion between the proximal end portion of the protective sheath and the proximal end portion of the elongated body.

4. The foreign object removal device according to claim 1, wherein a minimum protrusion amount of the screw protruding from the distal end opening of the protective sheath at the time of rotation of the screw is set to be longer than one-half of the interval of the screw, the one-half of the interval of the screw being a distance along the rotational center axis of the screw between the distal end point of the screw and a second side point of the screw with the second side point of the screw being shifted 90 degrees from the distal end point of the screw along the rotational direction of the screw.

5. The foreign object removal device according to claim 1, wherein a length of a portion of the screw housed in the lumen from the distal end opening at the time of the rotation of the screw is greater than the interval of the screw.

6. The foreign object removal device according to claim 1, further comprising:
 a contrast marker having a radiation contrast property, and which is attached to a proximal portion of the screw.

7. The foreign object removal device according to claim 1, wherein the screw has a pair of side edges that form the radially outer edge portion of the screw, the pair of side edges having a twisted shape wound in a spiral shape.

8. The foreign object removal device according to claim 7, further comprising:
 a twisted surface forming both surfaces of the flat plate is present between the pair of side edges, and the twisted surface forms a spiral flow path.

9. The foreign object removal device according to claim 8, wherein the twisted surface is continuous with a smooth surface without a columnar core at a rotational center of the screw.

10. The foreign object removal device according to claim 7, wherein the pair of side edges form a double spiral that twists, while sandwiching a rotation center axis of the screw.

11. The foreign object removal device according to claim 1, wherein a distance between the radially outer edge portion of the screw and an inner diameter of the protective sheath is 2.5% to 7.5% of the inner diameter of the protective sheath.

12. The foreign object removal device according to claim 1, wherein a distance from the radial outer edge portion of the screw to an inner surface on the rotational center axis of the screw is at least ⅓ of a diameter of the screw.

13. A foreign object removal device comprising:
a protective sheath;
a shaft capable of being inserted into a living body lumen; and
a screw which is provided at a distal end portion of the shaft, the screw having a shape in which a flat plate is twisted, and wherein the screw is configured to rotate integrally with the shaft;
a maximum protrusion amount of the screw protruding from a distal end opening of the protective sheath at a time of rotation of the screw being set to be less than an interval of the screw, the interval of the screw being a distance along a rotational center axis of the screw between a distal end point of the screw and a first side point of the screw with the first side point of the screw being shifted 180 degrees from the distal end point of the screw along a rotational direction of the screw; and
wherein the distal end point is connected to a distal end edge, the distal end edge being a portion of the screw that forms an edge portion on a distal end side from the rotational center axis of the screw to a side edge of the screw, and wherein the side edge forms a radially outer edge portion of the screw.

14. The foreign object removal device according to claim 13, wherein a rotational center of the screw is recessed in a proximal end direction at a distal end of the screw.

15. The foreign object removal device according to claim 13, wherein a proximal end portion of the protective sheath and a proximal end portion of the shaft connected to each other so as to be movable relative to each other, and an adjusting mechanism configured to adjust a protrusion amount of the screw is provided at an interlock portion between the proximal end portion of the protective sheath and the proximal end portion of the shaft.

16. The foreign object removal device according to claim 13, wherein a minimum protrusion amount of the screw protruding from the distal end opening of the protective sheath at the time of rotation of the screw is set to be longer than one-half of the interval of the screw, the one-half of the interval of the screw being a distance along the rotational center axis of the screw between the distal end point of the screw and a second side point of the screw with the second side point of the screw being shifted 90 degrees from the distal end point of the screw along the rotational direction of the screw.

17. The foreign object removal device according to claim 13, wherein a length of a portion of the screw housed in the lumen from the distal end opening at the time of the rotation of the screw is greater than the interval of the screw.

* * * * *